United States Patent
Dahl et al.

(10) Patent No.: US 11,397,167 B2
(45) Date of Patent: Jul. 26, 2022

(54) LOCAL SPEED OF SOUND ESTIMATION METHOD FOR MEDICAL ULTRASOUND

(71) Applicant: The Board of Trustees of the Leland Stanford Junior University, Palo Alto, CA (US)

(72) Inventors: Jeremy Joseph Dahl, Palo Alto, CA (US); Scott S. Hsieh, Anaheim, CA (US); Marko Jakovljevic, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1112 days.

(21) Appl. No.: 15/821,040

(22) Filed: Nov. 22, 2017

(65) Prior Publication Data

US 2018/0143165 A1 May 24, 2018

Related U.S. Application Data

(60) Provisional application No. 62/425,598, filed on Nov. 22, 2016.

(51) Int. Cl.
*G01N 29/07* (2006.01)
*A61B 8/08* (2006.01)
(Continued)

(52) U.S. Cl.
CPC ........... *G01N 29/07* (2013.01); *A61B 8/4483* (2013.01); *A61B 8/5269* (2013.01);
(Continued)

(58) Field of Classification Search
CPC .. G01N 29/07; G01N 29/024; G01N 29/4418; G01N 29/449; G01N 2291/011;
(Continued)

(56) References Cited

U.S. PATENT DOCUMENTS

2012/0004551 A1* 1/2012 Katsuyama .............. A61B 8/14
600/443
2012/0259225 A1* 10/2012 Tashiro .................. A61B 8/469
600/443
(Continued)

OTHER PUBLICATIONS

Byram, B. et al., "A Method for Direct Localized Sound Speed Estimates Using Registered Virtual Detectors," Ultrasonic Imaging. 2012, 34(3). p. 159-180 (Year: 2012).*
Anderson, M., et al. "The direct estimation of sound speed using pulse-echo ultrasound", Acoustical Society of America. 104, 1998. p. 3099-3106 (Year: 1998).*
(Continued)

*Primary Examiner* — Catherine B Kuhlman
*Assistant Examiner* — Sean A Frith
(74) *Attorney, Agent, or Firm* — Lumen Patent Firm

(57) ABSTRACT

Measuring local speed of sound for ultrasound by inducing ultrasound waves in a subject by focusing an ultrasound beam, using an ultrasound Tx transducer to propagate waves from a focal point to the surface, measuring a time of arrival of the waves using at least three single Rx transducer surface elements, signal traces recorded on individual Rx transducers are evenly sampled in time, an average speed of sound equals an arithmetic mean of local sound-speed values sampled along a wave path, each Rx transducer outputs a separate arrival time of the waves, computing a local speed of sound ($c_i$) of waves from an average speed of sound ($c_{avg}$) using a computer that receives arrival times, where $$c_{avg} = \frac{1}{N}\sum_{i=1}^{N} c_i,$$

where $c_i = d_i/T_s$, $d_i$ is the length a tissue traveled during one sampling period $T_s$, and using $c_i$ to differentiate human disease, or with ultrasound measurements to differentiate degrees of human disease.

13 Claims, 9 Drawing Sheets

(51) Int. Cl.
*A61B 8/00* (2006.01)
*G01N 29/024* (2006.01)
*G01N 29/44* (2006.01)

(52) U.S. Cl.
CPC ......... *G01N 29/024* (2013.01); *G01N 29/449* (2013.01); *G01N 29/4418* (2013.01); *G01N 2291/011* (2013.01); *G01N 2291/02466* (2013.01); *G01N 2291/02475* (2013.01); *G01N 2291/044* (2013.01)

(58) Field of Classification Search
CPC .......... G01N 2291/02466; G01N 2291/02475; G01N 2291/044; A61B 8/4483; A61B 8/5269
See application file for complete search history.

(56) References Cited

U.S. PATENT DOCUMENTS

| | | | | |
|---|---|---|---|---|
| 2013/0188196 | A1* | 7/2013 | Kang | G01B 9/02072 356/479 |
| 2014/0094702 | A1* | 4/2014 | Kim | A61B 8/0858 600/438 |
| 2016/0317121 | A1* | 11/2016 | Frenz | A61B 8/085 |
| 2016/0363561 | A1* | 12/2016 | Selbekk | G01N 29/032 |
| 2017/0238898 | A1* | 8/2017 | Waag | G01S 15/8993 |
| 2017/0265845 | A1* | 9/2017 | Tsushima | A61B 8/5223 |
| 2017/0363725 | A1* | 12/2017 | Ignjatovic | G01S 15/8915 |
| 2018/0263595 | A1* | 9/2018 | Goksel | A61B 8/5207 |

OTHER PUBLICATIONS

Ivancevich, N., et al. "Comparison of 3-D multi-lag cross-correlation and speckle brightness aberration correction algorithms on static and moving targets", IEEE Trans Ultrason Ferroelectr Freq Control, 2009. 56(10). p. 1-23 (Year: 2009).*

Shin, H., et al. "Estimation of average speed of sound using deconvolution of medical ultrasound data", Ultrasound in Medicine & Biology, 2010. 36(4). p. 623-636 (Year: 2010).*

Lin, L., et al. "Sellnv—An algorithm for selected inversion of a sparse symmetric matrix", ACM Transactions on Mathematical Software, vol. 37(4). 2011. p. 40:1-40:19 (Year: 2011).*

An Axial Velocity Estimator for Ultrasound Blood Flow Imaging, Based on a Full Evaluation of the Doppler Equation by Means of a Two-Dimensional Autocorrelation Approach, IEEE Transactions on Ultrasonics, Ferroelectrics, and Frequency Control, vol. 42, No. 4, T. Loupas, et al.

The direct estimation of sound speed using pulse-echo Ultrasound, J. Acoust. Soc. Am. 104 (5), Nov. 1998 (3099-3016), E. Trahey.

Time-shift compensation of ultrasonic pulse focus degradation using least-mean square error estimates of arrival time, The Journal of the Acoustical Society of America 95, 542 (1994), Dong-Lai Liu, and Robert C. Waag.

Computed Ultrasound Tomography in Echo Mode for Imaging Speed of Sound Using Pulse-Echo Sonography: Proof of Principle, Ultrasound in Med. & Biol., vol. 41, No. 1, pp. 235-250, 2015, M, Jaeger, et al.

Adaptive Imaging and Spatial Compounding in the Presence of Aberration, ieee transactions on ultrasonics, ferroelectrics, and frequency control, vol. 52, No. 7, Jul. 2005, Jeremy J. Dahl, et al.

* cited by examiner

LOCAL SPEED OF SOUND ESTIMATION METHOD FOR MEDICAL ULTRASOUND

CROSS-REFERENCE TO RELATED APPLICATIONS

This application claims priority from U.S. Provisional Patent Application 62/425,598 filed Nov. 22, 2016, which is incorporated herein by reference.

STATEMENT OF GOVERNMENT SPONSORED SUPPORT

This invention was made with Government support under contract EB015506 and HD086252 awarded by the National Institutes of Health. The Government has certain rights in the invention.

FIELD OF THE INVENTION

The current invention generally relates to using ultrasound imaging in medicine. More specifically, the invention relates to using said localized speed of sound measurements to differentiate a states of human disease.

BACKGROUND OF THE INVENTION

Speed of sound (SoS) in a medium influences important aspects of ultrasound imaging including travel-time and strength of backscattered echoes. Conventional ultrasound (B-mode) images are reconstructed assuming a constant speed of sound in tissue. In the presence of sound-speed inhomogeneities, this assumption is not true as different parts of the wavefront will travel at different speeds and the focal delays based on a constant sound-speed value may result in incoherent summation of signals across the aperture, and a subsequent loss of image resolution.

Knowledge of speed of sound along a wave propagation path allows one to more accurately predict the arrival times of backscattered signals, so that they can be summed in-phase yielding a higher quality ultrasound image. Knowledge of the speed of sound in tissue can also be used for diagnostic purposes directly, i.e. to help differentiate between healthy and diseased tissues. For example, studies in excised human and animal livers have shown a markedly lower sound speed in livers that suffer from non-alcoholic fatty liver disease (NAFLD) compared to healthy livers. In particular, an average SoS of 1528 m/s in fatty liver, compared to 1567 m/s in normal liver has been shown. Also, it was shown that the speed of sound decreased by an average of 2.3 to 2.5 m/s per % fat concentration. While B-mode ultrasound is commonly used in identifying NAFLD, B-mode alone is not sensitive for liver fat concentrations lower than 30%. SoS measurements obtained from the same pulse-echo data that is used to reconstruct a B-mode image could help improve early diagnosis and staging of the disease.

Current SoS estimators yield poor accuracy in the presence of inhomogeneities and/or are not suited for pulse-echo scanner architectures. The gross sound-speed estimators, which measure the average speed of sound between the face of the transducer and focus are particularly sensitive to layers of subcutaneous fat and connective tissue. These estimators include techniques based on the apparent shift from two angles, beam tracking, transaxial compression, phase variance, and on the echo arrival times at receive aperture. For example, the average SoS estimator previously taught yields highly accurate estimates in the homogeneous media (bias less than 0.2% and standard deviation less than 0.52%) and can be implemented on a clinical pulse-echo system. However, this instance's estimates suffer from large bias and variance when inhomogeneous media are in the propagation path; in a two-layer phantom composed of water and agar-graphite, measured biases exceeded 300 m/s at depths just a few millimeters below the layer boundary.

Ultrasound computed tomography methods can produce highly accurate and localized (i.e. with high spatial resolution) SoS estimates of complex media, but these techniques require the target tissue to be inside a ring of transducer elements, which narrows their use to breast imaging. There are pulse-echo-based estimators that are capable of providing localized sound speed estimates such as the crossed-beam method, the modified beam tracking method, registered virtual detectors, and ultrasound computed tomography in echo mode. All of these methods can be implemented on conventional ultrasound arrays, except for the modified beam-tracking method, which requires two transducers. However, while these local sound-speed estimators show reduced bias in the presence of inhomogeneities compared to the gross sound speed estimators, their error is still too large to detect SoS changes with fat concentration for successful NAFLD diagnosis and staging. In one example, the method of registered virtual detectors is shown to have a bias as large as 16% of the local sound-speed value with a 24 dB signal-to-noise ratio. Further, the local SoS maps (estimated via a model-based approach) show well-resolved circular lesions, but the lesion contrast and estimate statistics are not reported.

What is needed is a method to estimate sound speed in a localized region of tissue with high accuracy that can be implemented on a pulse-echo ultrasound system.

SUMMARY OF THE INVENTION

To address the needs in the art, a method of measuring local speed of sound for medical ultrasound is provided that includes inducing ultrasound waves in a subject under test by focusing an ultrasound beam at a region of interest, using an ultrasound Tx transducer, where the ultrasound waves propagate from an ultrasound Tx focal point to a surface of the subject under test, measuring a time of arrival of the propagating ultrasound waves, using at least three single ultrasound Rx transducer elements disposed on the surface of the subject under test, where signal traces recorded on individual ultrasound Rx transducers are uniformly sampled in time, where an average speed of sound in the subject under test equals an arithmetic mean of local sound-speed values sampled along a propagation path of the ultrasound waves, where each ultrasound Rx transducer outputs a separate arrival time of the propagating ultrasound waves, computing a local speed of sound ($c_i$) of the propagating ultrasound waves from an average speed of sound ($c_{avg}$) of the propagating ultrasound waves using a computer that receives the output arrival times, where $c_{avg}$ equals the arithmetic mean of the $c_i$ values sampled along a wave propagation path according to $$c_{avg} = \frac{1}{N}\sum_{i=1}^{N} c_i,$$

where $c_i = d_i/T_s$, where $d_i$ is the length of a tissue segment traveled during one sampling period $T_s$, and using $c_i$ to differentiate states of human disease, or using the $c_i$ in conjunction with other ultrasound measurements to improve a differentiation between mild and severe forms of human disease.

According to one aspect of the invention, where when signal traces recorded on the individual ultrasound Rx transducers are uniformly sampled in space, an average slowness in the subject under test equals an arithmetic mean of local slowness values sampled along a propagation path of the ultrasound.

In a further aspect of the invention, the $c_{avg}$ arrival time is calculated by fitting a parabolic profile to ultrasound Rx data, that defines a geometric distance from the ultrasound Tx focal point to at least three single ultrasound Rx transducer elements.

In another aspect of the invention, an arrival-time profile of the propagating ultrasound waves across all the ultrasound Rx transducer elements is formed from time-delays determined by a multi-lag least-squares estimation algorithm.

In yet another aspect of the invention, an arrival-time profile of the propagating ultrasound waves is determined from elements of the Tx transducer.

According to one aspect of the invention, the local sound speed estimates from multiple wave propagation angles are averaged together.

In another aspect of the invention, a system of linear equations $\underline{c}_{avg}=A\underline{c}_{local}+\underline{\varepsilon}_{meas}$ is formed, where each row of a model matrix A encodes a single measurement of the average speed of sound in vector $\underline{c}_{avg}$, where a vector $c_{local}$ contains the local sound speeds $c_i$ to be solved for, where $\underline{\varepsilon}_{meas}$ is a vector of measurement errors to be minimized. Here, in one aspect, a gradient descent algorithm is used to solve the system of linear equations. In a further aspect, the matrix A is triangular and a direct inversion is used to solve the system of linear equations. In another aspect, the matrix A encodes speeds of sound that are averaged along multiple directions of propagation. In yet another aspect $c_{local}$ is solved for multiple directions of propagation and then averaged. According to a further aspect, the minimization of the vector of measurement $\underline{\varepsilon}_{meas}$ is performed with the $l_1$ norm or $l_2$ norm. In a further aspect, image noise is reduce by using additional regularization of the spatial variation of the $c_{local}$. According to one aspect, signal traces recorded on the individual ultrasound Rx transducers are uniformly sampled in space and slowness at a voxel $\sigma_i=1/c_i$ replaces the $c_i$ in the system of linear equations.

BRIEF DESCRIPTION OF THE DRAWINGS

FIGS. 8A-8B show sound speed estimates from the speckle phantom with and without aberrating layers in the acoustic path. (8A) The Anderson method. (8b) The local SoS estimator according to the current invention. From left to right the data was acquired directly on the phantom, through a 4 mm-thick layer of porcine muscle tissue, and through a 10 mm-thick tissue-layer. The Anderson estimates obtained through the 4 mm tissue layer are higher than the Anderson estimates for the no-aberrator case, while the local SoS estimates are similar between the two acquisitions. For the acquisition through the 10 mm aberrator, the local SoS estimates are computed starting at 20 mm depth in order to omit the data corrupt by reverberation clutter. The 5-by-5 mm region of interest used to compute the estimate statistics (Table V) is denoted with a red square, according to the current invention.

DETAILED DESCRIPTION

Incorporated by reference herein in its entirety is T. Loupas, J. T. Powers, and R. W. Gill. "An Axial Velocity Estimator for Ultrasound Blood Flow Imaging, Based on a Full Evaluation of the Doppler Equation by Means of a Two-Dimensional Autocorrelation Approach," IEEE Transactions on Ultrasonics, Ferroelectrics, and Frequency Control 42(4):672-88, 1995, which teaches a velocity estimator, referred to as the 2D autocorrelator, which differs from conventional Doppler techniques in two respects: the derivation of axial velocity values by evaluating the Doppler equation using explicit estimates of both the mean Doppler and the mean RF frequency at each range gate location; and, the 2D nature (depth samples versus pulse transmissions) of processing within the range gate. The estimator's output can be calculated by evaluating the 2D autocorrelation function of the demodulated (baseband) backscattered echoes at two lags. A full derivation and mathematical description of the estimator is presented, based on the framework of the 2D Fourier transform. The same framework is adopted to analyze two other established velocity estimators (the conventional 1D autocorrelator and the crosscorrelator) in a unifying manner, and theoretical arguments as well as experimental results are used to highlight the common aspects of all three estimators. In addition, a thorough performance evaluation is carried out by means of extensive simulations, which document the effect of a number of factors (velocity spread, range gate length, ensemble length, noise level, transmitted bandwidth) and provide an insight into the optimum parameters and trade-offs associated with individual algorithms. Overall, the 2D autocorrelator is shown to offer the best performance in the context of the specific simulation conditions considered here. Its superiority over the crosscorrelator is restricted to cases of low signal-to-noise ratios. However, the 2D autocorrelator always outperforms the conventional 1D autocorrelator by a significant margin. These comparisons, when linked to the computational requirements of the proposed estimator, suggest that it combines the generally higher performance of 2D broadband time-domain techniques with the relatively modest complexity of 1D narrowband phase-domain velocity estimators.

Further incorporated by reference herein in its entirety is Martin E. Anderson and Gregg E. Trahey "The direct estimation of sound speed using pulse-echo Ultrasound" J. Acoust. Soc. Am. 104 (5), November 1998 (3099-3016) teaches a method for the direct estimation of the longitudinal speed of sound in a medium. This estimator derives the speed of sound through analysis of pulse-echo data received across a single transducer array following a single transmission, and is analogous to methods used in exploration seismology. A potential application of this estimator is the dynamic correction of beamforming errors in medical imaging that result from discrepancy between the assumed and actual biological tissue velocities. The theoretical basis of this estimator is described and its function demonstrated in phantom experiments. Using a wire target, sound-speed estimates in water, methanol, ethanol, and n-butanol are compared to published values. Sound-speed estimates in two speckle-generating phantoms are also compared to expected values. The mean relative errors of these estimates are all less than 0.4%, and under the most ideal experimental conditions are less than 0.1%. The relative errors of estimates based on independent regions of speckle-generating phantoms have a standard deviation on the order of 0.5%. Simulation results showing the relative significance of potential sources of estimate error are presented. The impact of sound-speed errors on imaging and the potential of this estimator for phase aberration correction and tissue characterization are also discussed.

Also incorporated by reference in its entirety is Dong-Lai Liu, and Robert C. Waag "Time-shift compensation of ultrasonic pulse focus degradation using least-mean square error estimates of arrival time" The Journal of the Acoustical Society of America 95, 542 (1994), which teaches focus degradation produced by abdominal wall has been compensated using a least-mean-square error estimate of arrival time. The compensation was performed on data from measurements of ultrasonic pulses from a curved transducer that emits a hemispheric wave and simulates a point source. The pulse waveforms were measured in a two-dimensional aperture after propagation through a water path and after propagation through different specimens of human abdominal wall. Time histories of the virtual point source were reconstructed by removing the time delays produced by geometric path differences and also removing time shifts produced by propagation inhomogeneities in the case of compensation finding the complex amplitudes of the Fourier harmonics across the aperture, calculating the Fraunhofer diffraction pattern of each harmonic, and summing the patterns. This process used a least-mean-square error solution for the relative delay expressed in terms of the arrival time differences between neighboring points and included an algorithm to determine arrival time differences when correlation based estimates were unsatisfactory due to dissimilarity of neighboring waveforms. Comparisons of reconstructed time histories in the image plane show that the −10-dB effective radius of the focus for reception through abdominal wall without compensation for inhomogeneities averaged 4 to 8% greater than the corresponding average effective radius for ideal waveforms, while time-shift compensation reduced the average −10-dB effective radius to a value that is only 4% greater than for reception of ideal waveforms. The comparisons also indicate that the average ratio of energy outside an ellipsoid defined by the −10-dB effective widths to the energy inside that ellipsoid is 1.81 mm for uncompensated tissue path data and that time-shift compensation reduced this average to 0.93 mm, while the corresponding average for ideal waveforms was found to be 0.35 mm. These results show that time-shift compensation yields a significant improvement over the uncompensated case although other factors must be considered to achieve an ideal diffraction limited focus.

Incorporated by reference in its entirety herein is J. J. Dahl, D. A. Guenther, and G. E. Trahey, "Adaptive imaging and spatial compounding in the presence of aberration," IEEE Trans Ultrason Ferroelect Freq Contr, vol. 52, no. 7, pp. 1131-1144, 2005, which teaches how spatial compounding reduces speckle and increases image contrast by incoherently averaging images acquired at different viewing angles. Adaptive imaging improves contrast and resolution by compensating for tissue-induced phase errors. Aberrator strength and spatial frequency content markedly impact the desirable operating characteristics and performance of these methods for improving image quality. Adaptive imaging, receive-spatial compounding, and a combination of these two methods are presented in contrast and resolution tasks under various aberration characteristics. All three imaging methods yield increases in the contrast-to-noise ratio (CNR) of anechoic cysts; however, the improvements vary depending on the properties of the aberrating layer. Phase correction restores image spatial frequencies, and the addition of compounding opposes the restoration of image spatial frequencies. Lesion signal-to-noise ratio (SNR), an image quality metric for predicting lesion detectability, shows that combining spatial compounding with phase correction yields the maximum detectability when the aberrator strength or spatial frequency content is high. Examples of these modes are presented in thyroid tissue.

The current invention provides a model and a method to estimate sound speed in a localized region of tissue with high accuracy implemented on a pulse-echo ultrasound system. The model provide herein relates the average SoS between the transducer and focus to the local SoS values along the wave propagation path. In one embodiment of this implementation of the local SoS estimator, the average SoS from arrival-time profiles is computed using the method by Anderson and Trahey. The current SoS model is validated using the ideal and noisy arrival-times that are synthesized directly from known SoS maps. Demonstrated herein is the local SoS estimator using synthetic aperture ultrasound signals from fullwave simulations and phantom experiments in homogeneous and two-layer media. In all cases, standard deviation and bias of the local SoS estimates are measured and compared to the estimate statistics obtained for the Anderson method.

Figure 1:
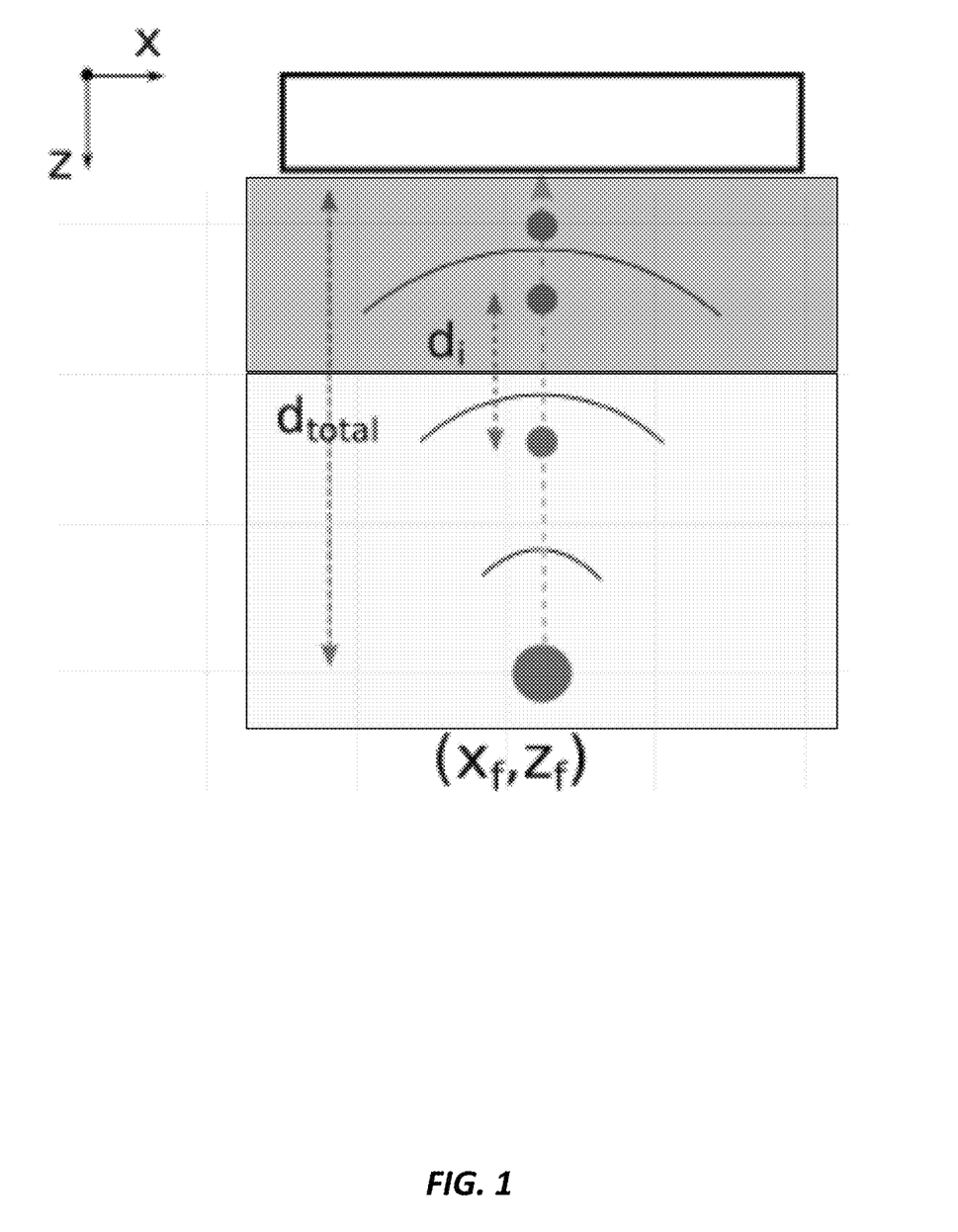
FIG. 1 shows a schematic drawing of the wave propagation from focus to the transducer surface under the assumption of even sampling in time. Due to differences in the local speed of sound, individual distances a traveled between the time samples are different, according to one embodiment of the invention.

To derive a model for the local speed of sound (SoS), it is assumed that the signal traces recorded on individual elements are uniformly sampled in time, while the distances traveled between the samples might vary due to differences in the local speed of sound. This assumption is consistent with how most ultrasound scanners collect the data. The total distance traveled by the wave between the focus and transducer can then be expressed as $$d_{total} = \sum_{i=1}^{N} d_i, \quad (1)$$

where $d_i$ is the length of tissue segment i traveled during one sampling period $T_s$. Given that $d_i = c_i T_s$, where $c_i$ is the local SoS, it follows that $$c_{avg}(NT_s) = \sum_{i=1}^{N} c_i T_s, \quad (2)$$

$$c_{avg} = \frac{1}{N} \sum_{i=1}^{N} c_i. \quad (3)$$

In other words, the average speed of sound equals the arithmetic mean of the local sound-speed values sampled along a wave propagation path. The starting assumption for the model according to the current invention in (1) is also shown in FIG. 1.

When the ultrasound signal is uniformly sampled in space instead in time, the expression $t_{total} = \sum_{i=1}^{N} t_i$ is used in place of equation (1). In this embodiment, in order to estimate the speed of sound along a path, it may be necessary to invert speed of sound and instead solve first for the "slowness," or a (reciprocal of speed, or 1/c). Specifically, the average speed of sound between any two points along a straight-line path is related to the localized speed of sound at every point in that path by $$\frac{1}{c_{avg}} = \frac{1}{N} \sum_{k=1}^{K} \frac{1}{c_i} \quad (4)$$

where in the above equation the distances between the localized points i are equal.

The relationships in (3) and (4) can be generalized as linear system of equations $$\underline{c}_{avg} = A \underline{c}_{local} + \underline{\varepsilon}_{meas}, \quad (5a)$$

or $$\underline{\sigma}_{avg} = A \underline{\sigma}_{local} + \underline{\varepsilon}_{meas}, \quad (5b)$$

where each row of model matrix A encodes a single measurement of average SoS and $\underline{\varepsilon}_{meas}$ is a vector of measurement errors. For average SoS measurements collected along the same direction of wave propagation (FIG. 1), A becomes a lower triangular matrix and (5) can be solved for $\underline{c}_{avg}$ via direct inversion. The model matrix A, however, can encode more complex scenarios, such as when multiple directions or angles of wave propagation are included in the model. In this case, A is more complex (than the lower triangular matrix) and numeric solvers may be necessary. Similarly, individual model matrices A can each encode a different direction or angle of wave propagation, and these model matrices and the associated speed of sound (or slowness) can be solved individually, with the result of each solution averaged together. By including or averaging these multiple directions or angles of propagation, the variation in the estimates can be reduced.

In the matrix framework, the method of gradient descent is particularly simple, and is closely related to the Algebraic Reconstruction Technique (ART) employed in early CT scanners. Briefly, in gradient descent, the reconstruction is initialized with a uniform speed of sound. Local sound speeds (or slowness values) along a the ray path are added to find the average speed of sound (or slowness) expected from the current reconstruction, and compare it to the measured average sound speed value. Let the difference between the measured speed of sound (or slowness) and its expected value be a quantity d. Then, q*d/p is added (or "back projected") to each pixel in the ray path, where q is a tuning constant chosen for convergence and p is the number of pixels in the ray path. This is done over all average sound speed measurements, and repeated several times until convergence.

In the following, the average SoS measurements have been obtained via the method by Anderson and Trahey. With this approach, the average SoS from a focus point to the transducer surface is computed using the corresponding times of arrival at the transducer elements.

The arrival times at the individual elements are inferred from time delays between the neighboring element signals. Specifically, signals from a speckle target retain high degree of similarity among the neighboring elements and can be expressed as $$s_{x_1}(t) = s_{x_2}(t + t\delta_{x_1 x_2}) + \varepsilon_{x_1 x_2}, \quad (6)$$

where $s_{x_1}$ and $s_{x_2}$ are signal traces recorded at locations $x_1$ and $x_2$ in the aperture (typically not more than five elements apart), $\delta_{x_1, x_2}$ is the associated time delay, and E is Gaussian noise. To measure the delays, the corresponding signal traces are cross-correlated around a specific time or depth. The arrival-time profile of the signals across the entire array is then formed from these time delays using the multi-lag least-squares approach as outlined by Liu and Waag and Dahl et al. In summary, the delays are expressed in terms of the arrival times at the individual elements $$d_{x_1, x_2} = \hat{\delta}_{x_1, x_2} = t_{x_1} - t_{x_2} + \varepsilon_{x_1, x_2}, \quad (7)$$

which can be written in the matrix form as $$\underbrace{\begin{bmatrix} 1 & -1 & 0 & 0 & \ldots & 0 \\ 1 & 0 & -1 & 0 & \ldots & 0 \\ 1 & 0 & 0 & -1 & \ldots & 0 \\ \ldots & \ldots & \ldots & \ldots & \ldots & \ldots \\ 0 & 0 & \ldots & 0 & 1 & -1 \end{bmatrix}}_{M} \underbrace{\begin{bmatrix} t_1 \\ t_2 \\ t_3 \\ \vdots \\ t_{N-1} \end{bmatrix}}_{t} + \underbrace{\begin{bmatrix} \varepsilon_{1,1} \\ \varepsilon_{1,2} \\ \varepsilon_{1,3} \\ \vdots \\ \varepsilon_{N-1,L} \end{bmatrix}}_{\varepsilon} = \underbrace{\begin{bmatrix} d_{1,1} \\ d_{1,2} \\ d_{1,3} \\ \vdots \\ d_{N-1,L} \end{bmatrix}}_{d}, \quad (8)$$

In equation (8), each row of the model matrix M encodes a pair of receive elements, N is the number of elements in the array, vectors $\underline{d}$ and $\underline{\varepsilon}$ contain all measured delays and the associated errors, respectively, and the vector $\underline{t}$ contains the arrival times. The vector $\underline{t}$ is estimated via the least-squares solution $$\hat{\underline{t}} = (M^T M)^{-1} M^T \underline{d}. \quad (9)$$

For a medium with the uniform speed of sound c, the arrival times t can be also expressed in a closed-form, based on the geometric distance between the focus and a transducer element $$t(x_e) = \frac{\sqrt{(x_e - x_f)^2 + y_f^2 + z_f^2}}{c}, \quad (10)$$

where $x_f$, $y_f$, and $z_f$ are coordinates of the focal point, $x_e$ is the x-coordinate of the transducer element and $y_e$ and $z_e$ are set to zero (i.e. the transducer runs parallel to the x-axis and is centered at the origin). The expression in 10 can be rewritten as the equation for parabola)

$$t^2(x_e) = p_1 x_e^2 + p_2 x_e + p_3, \quad (11)$$

with the coefficients $$p_1 = \frac{1}{c^2},$$

$$p_2 = -\frac{2x_f}{c^2},$$

$$p_3 = \frac{x_f^2 + y_f^2 + z_f^2}{c^2}.$$

Figure 2:
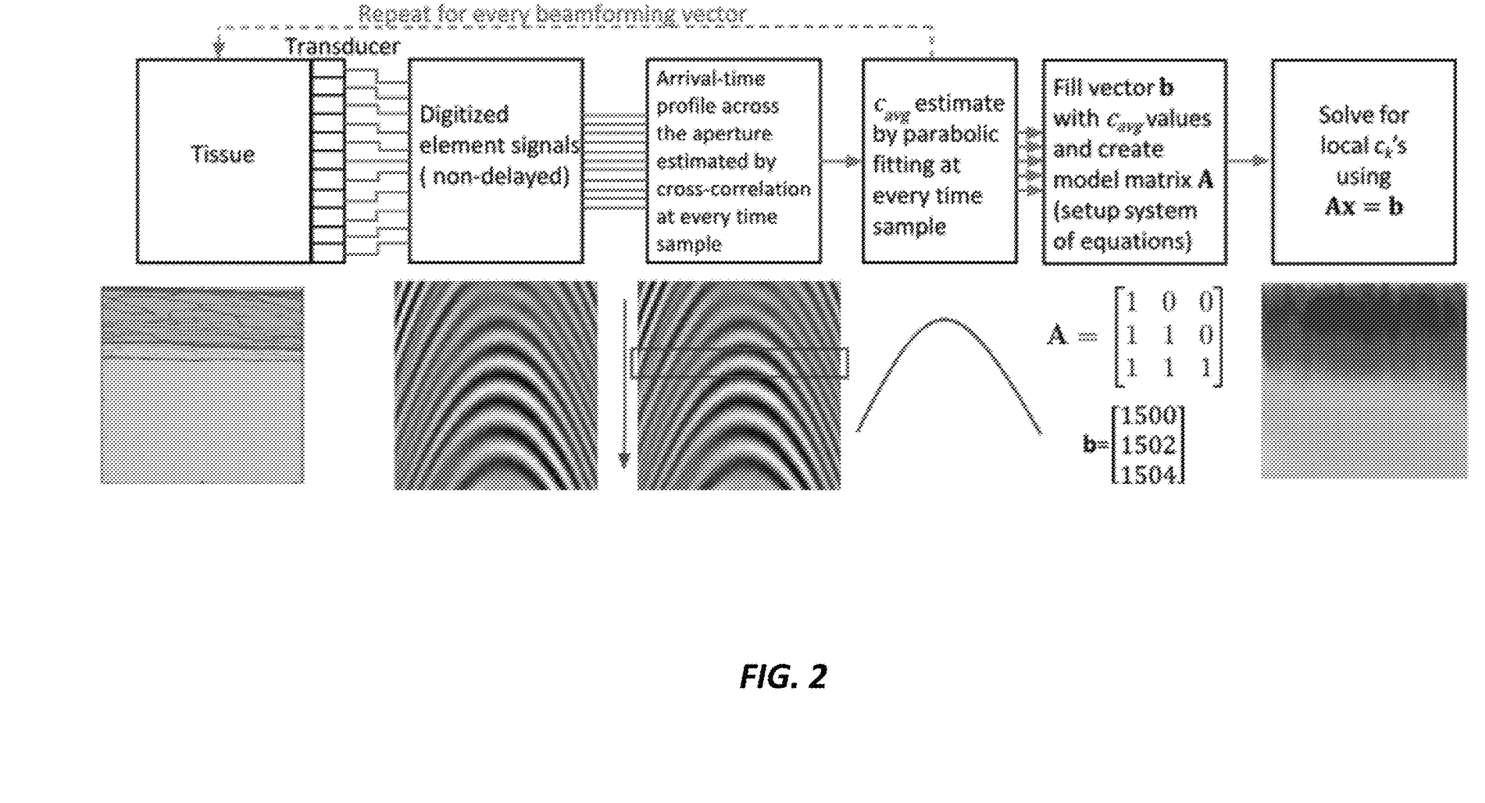
FIG. 2 shows a processing flow of the local sound speed estimator. The raw element signals are captured and the average speed of sound is estimated at every point by parabolic fitting of the square of the arrival time profile. The average speed of sound values are then used to compute the local sound speed estimates from the model in (5). Note that the images are for illustration purposes and do not represent actual data, according to one embodiment of the invention.

Therefore, the average speed of sound is estimated by fitting a parabola to the square of the arrival-time profile measured in (9), followed by taking the square root of the inverse of the coefficient $p_i$. As a variation of the technique by Anderson and Trahey, one embodiment of the invention uses a synthetic transmit aperture sequence to collect the data, and then utilize the principle of acoustic reciprocity to estimate the arrival-time profiles across the beamformed signals corresponding to different transmit elements. The resulting estimates are the same as those from the receive-element signals described previously. The use of beamformed data enables the estimation of arrival times (and average speed of sound) on a clinical scanner without significant modifications to the existing scanner architecture. In addition, the arrival-time profiles across the transmit elements are used to improve transmit focusing for subsequent iterations of the method without necessitating additional transmit events. The average SoS values estimated from the arrival-time profiles are used to solve for local sound speeds in (5). The workflow of the whole estimation process is diagrammed in FIG. 2.

The models in (11) and (5) have been validated against "synthetic" data obtained from known speed-of-sound maps. The maps each have two layers, a 15 mm-thick layer on top with the SoS of 1480 m/s, and the bottom layer with SoS of 1520, 1540, and 1570 m/s, respectively.

The exact arrival times were computed for each point in the map (to the transducer surface) by solving the following Eikonal equation:

$$\nabla(\phi(x)) = \frac{1}{c(x)}. \quad (13)$$

In (13), c(x) is the local sound-speed and ϕ(x) is the wave-propagation phase function, which can be interpreted as the minimum time required for a wave to travel from source to point x in space under a high-frequency approximation. The equation was solved for ϕ(x) numerically via a fast marching method.

The exact arrival times were used to compute the average SoS via Anderson's method for each point in the map. The local SoS values were then inferred from the average SoS according to (5); the method of gradient descent was used to solve the equation numerically. To assess inaccuracies in models (11) and (5) the mean and standard deviation were computed for both average and local sound-speed estimates.

To investigate error propagation in (5), the average SoS values were also generated directly from true sound speeds. The zero-mean, white, Gaussian noise with standard deviation of 5 m/s was added to mimic measurement variations due to thermal noise and speckle. The local SoS was then estimated from the synthetic average-SoS data using the method of gradient descent. Different levels of $l_2$ norm regularization were used in the numeric solver to reduce the noise in the final estimates.

Turning now to fullwave simulations, the signals received on the individual elements of a linear 1-D array were simulated while scanning homogeneous and two-layer phantoms. The signals were obtained using a fullwave simulation tool, which models 2-D acoustic wave propagation including the effects of non-linearity, attenuation, and multiple scattering (reverberation). In particular, a propagated medium is assigned a speed of sound, attenuation, density, and non-linearity maps, which allows us to define a ground truth for speed-of-sound estimation from complex imaging targets.

The homogeneous phantoms were created with 1480, 1540, and 1600 m/s speed of sound. The two-layer phantoms each consisted of a top layer, which had 1480 m/s speed of sound, and bottom layers with 1520, 1540, and 1570 m/s sound speeds, respectively. In order to simulate speckle, small local variations in speed of sound (average variation of 5% from the surroundings) were introduced throughout the modeled medium. The resulting point scatterers had a 40 μm diameter and were randomly distributed with average density of twelve scatterers per resolution cell. The rest of parameters (density, attenuation, and non-linearity) were uniform and the same for all phantoms.

Having specified the acoustic properties of phantoms, a transmit event was simulated for each of 128 array elements to create transmit synthetic aperture data sets. For each transmit, the simulation code was run to numerically solve the full-wave equation (via FDTD method) giving the pressure field across the grid at all times. Initial conditions for solving the equation were set by prescribing the transmit waveforms at a transmit element location. Receive element signals

TABLE I

Simulated transducer properties.

| Array Width | 19.2 mm |
|---|---|
| Number of Elements | 128 |
| Element Pitch | 0.15 mm |
| Center Frequency | 5 MHz |
| Bandwidth | 50% | were obtained by sampling the pressure field at the face of the transducer and convolving it with the axial transducer impulse response. Specifically, the transmit center frequency was set at 5 MHz and the transducer impulse response was set to yield a fractional bandwidth of 0.5. The total aperture width was 1.92 cm. Specifications of the modeled array are summarized in Table I.

The receive-element signals from each transmit event were used to beamform 128 receive lines steered perpendicular to the transducer surface (i.e. 0 degrees) and spaced apart by one $\lambda$. For each receive line, the principle of acoustic reciprocity was applied to compute the arrival times across transmit elements (as explained above), and then to estimate the average and local sound speeds following the procedure in FIG. 2. The arrival-time estimation was done iteratively five times. Using the same procedure as described here, 128 receive lines were beamformed at 4 other angles of wave propagation (−10, −5, 5, and 10 degrees) and used to compute local sound speeds.

Regarding phantom acquisitions, the experiments were also performed on a speckle generating phantom (Model 549, ATS, Bridgeport, Conn.) using a L12-3v linear array attached to a Verasonics™ Vantage 256 scanner. Complete synthetic aperture data was acquired without an aberrator and through a 4 mm and a 10 mm-thick layer of degassed porcine tissue placed directly under the transducer. The data was acquired at a transmit center-frequency of 7 MHz. The speckle generating phantom had a calibrated speed of sound of 1460 m/s. The porcine tissue samples contained skin, fat, muscle, and connective tissue and were used to mimic a subcutaneous aberrating layer that disrupts speed of sound estimates at the region of interest. The arrival time profiles were estimated across transmit elements (via the principle of acoustic reciprocity). The average and local sound speeds were then estimated following the procedure in FIG. 2.

Figure 3A:
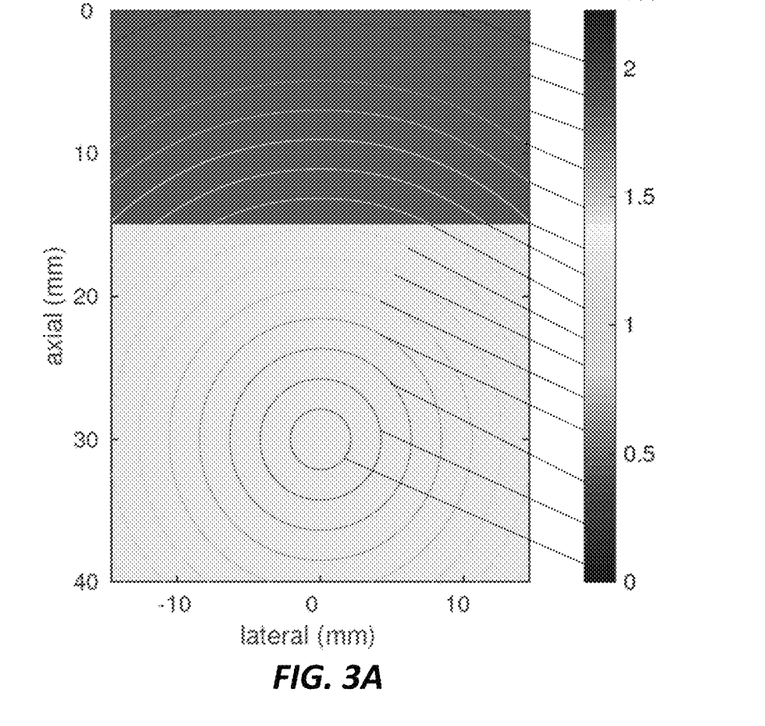
FIGS. 3A-3B show examples of one-way arrival times computed for a two-layer speed of sound map using the Eikonal equation in (13). Sound speed of the top layer is 1480 m/s and that of the bottom layer is 1520 m/s. (3A) Arrival-time contours for waves emanating from a focal point located in the center of FOV, at 30 mm depth. (3B) Arrival times corresponding to the cross-section of contours at the transducer surface. A second-order polynomial fit used to compute the average speed of sound (equation (11)) is an accurate model for the arrival-time profiles in this example, according to embodiments of the current invention.
Figure 3B:
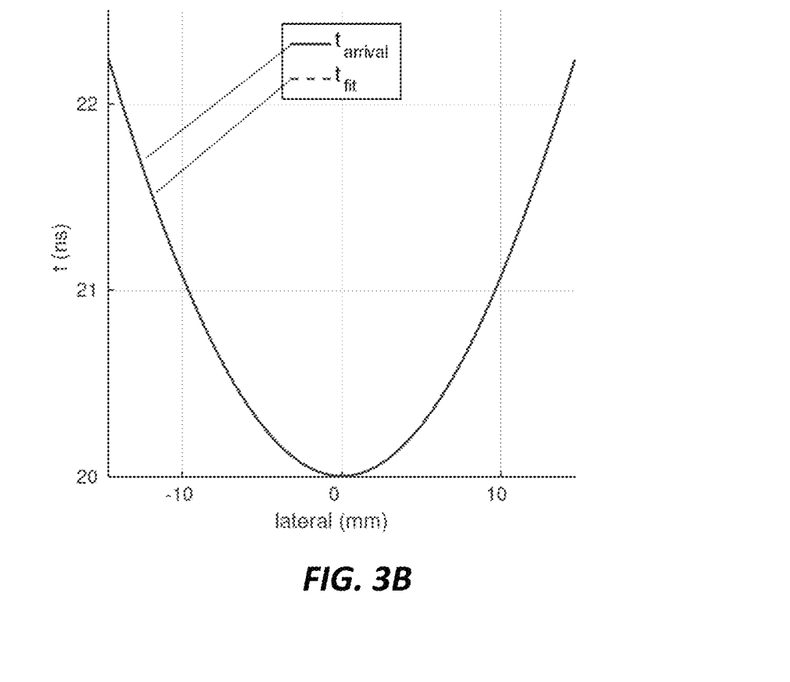

Turning now to the results, for the model validation, an example of one-way arrival times computed via the Eikonal equation in (13) is shown in FIGS. 3A-3B. In FIG. 3A, the arrival time contours are displayed over a two-layer speed of sound map to illustrate wavefronts originating from a focal point in the middle of FOV, at 30 mm depth. The speed of sound of the top layer is 1480 m/s and that of the bottom layer is 1520 m/s. The arrival times used to compute the average speed of sound via Anderson's method correspond to the cross-section of contours at the transducer surface. In FIG. 3B, the arrival times at the transducer surface are plotted together with the square root of the corresponding parabolic fit in equation (11). For the two-layer medium used in this example, the model in equation (11) does not deviate significantly from true arrival-time profiles.

Figure 4A:
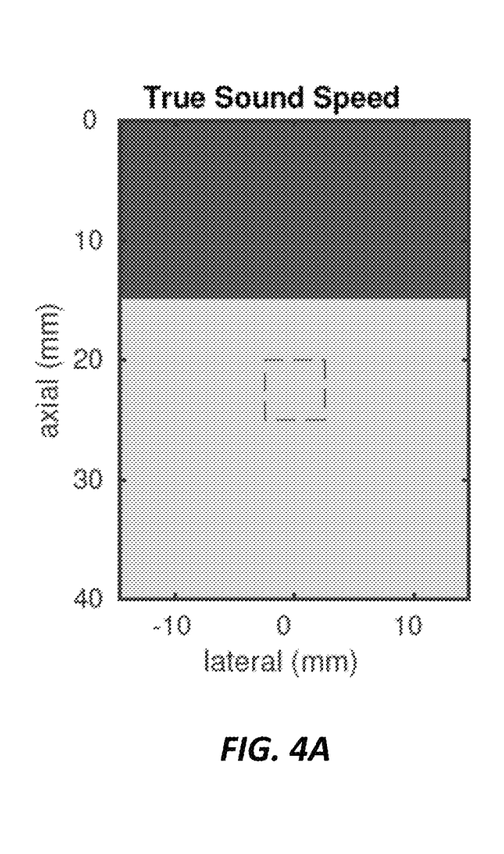
FIGS. 4A-4C show examples of two-layer SoS maps used to validate the models in (11) and (5). (4A) Ground-truth SoS map used to compute the exact one-way arrival times via the Eikonal equation. (4B) The corresponding average SoS estimates computed from the arrival times via Anderson's method. (4C) The corresponding local SoS estimates. When the arrival times are known, the local sound-speed estimates are close to ground truth. The region used to compute the mean and standard deviation of Anderson and local SoS estimates is denoted with a dashed square. The estimate statistics for all SoS maps are summarized in Table II, according to embodiments of the current invention.
Figure 4B:
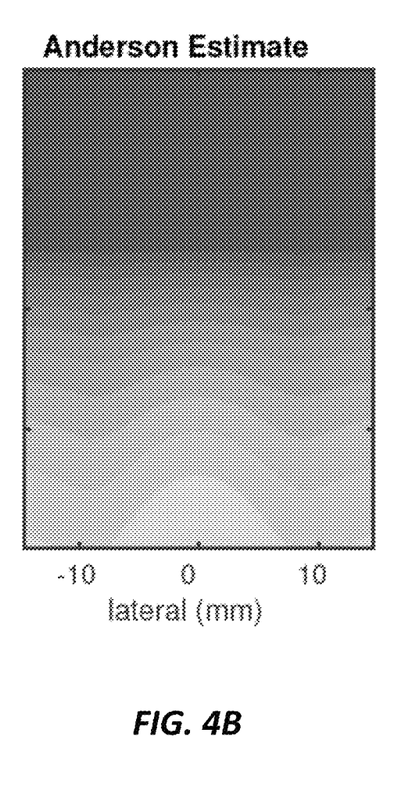
Figure 4C:
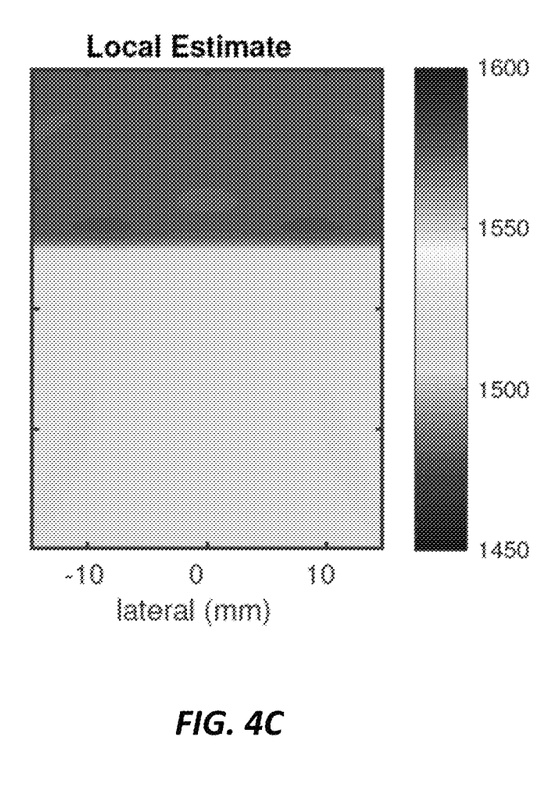

Average and local sound-speed estimates computed from the exact arrival times are displayed in FIG. 4 for the 1480/1520 m/s SoS map. The average (i.e. Anderson) SoS estimates gradually increase beyond 15 mm depth. The local SoS estimates show a clear separation between the two layers and are uniform within each layer. In other words, when the arrival times are measured exactly, the models in equations (11) and (5) yield local sound-speed estimates that are close to true SoS values. The statistics of SoS estimates computed using the exact arrival times are presented in Table II for all the two-layer SoS maps. The region-of-interest (ROI) used to compute the estimate statistics is shown in the first map in FIG. 4 using a red square. The bias of the Anderson estimates is not less than 26 m/s, and it increases as the difference in sound-speed between the two layers becomes larger. On the other hand, the local SoS estimates have a low bias (less than 5 m/s) and low standard deviation (0.3 m/s) that are consistent between the maps.

TABLE II

Bias and standard deviation of SoS estimates computed from the exact arrival times in two-layer media.

| | Sound Speed in Bottom Layer | | | | | |
|---|---|---|---|---|---|---|
| | 1520 m/s | | 1540 m/s | | 1570 m/s | |
| | Local | Anderson | Local | Anderson | Local | Anderson |
| mean | 1523.0 | 1493.8 | 1543.4 | 1500.3 | 1574.3 | 1509.9 |
| bias | 3.0 | −26.2 | 3.4 | −39.7 | 4.3 | −60.1 |
| ROI Std dev | 0.3 | 1.9 | 0.3 | 2.7 | 0.3 | 4.0 |

Figure 5A:
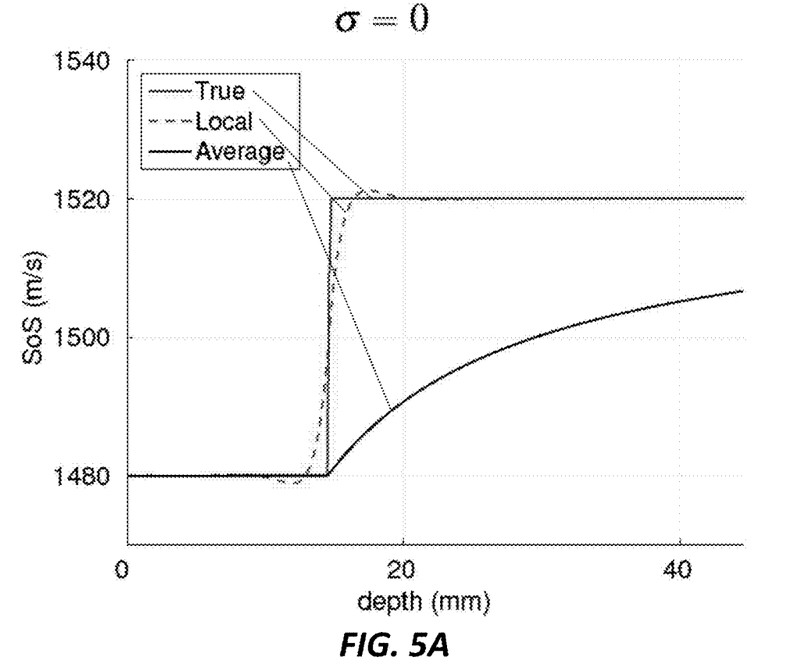
FIGS. 5A-5B show the impact of average sound speed measurement error on local sound speed estimates. When there is no noise in the synthetic data (the standard deviation is $\sigma=0$), the estimated local sound speed closely matches the true values. When Gaussian noise is added to the data ($\sigma=5$ m/s), the gradient descent solver increases the noise level, especially at large depths. Doubling the regularization term w, in the solver suppresses the noise in local SoS estimates, but blurs the boundary between the two layers. The standard deviation of local SoS estimates at the bottom layer (between 20 and 40 mm) is computed to be $\sigma_{wr}$ 12:5 m/s and $\sigma_{2wr}$ 5:6 m/s for the two regularization terms, respectively, according to the current invention.
Figure 5B:
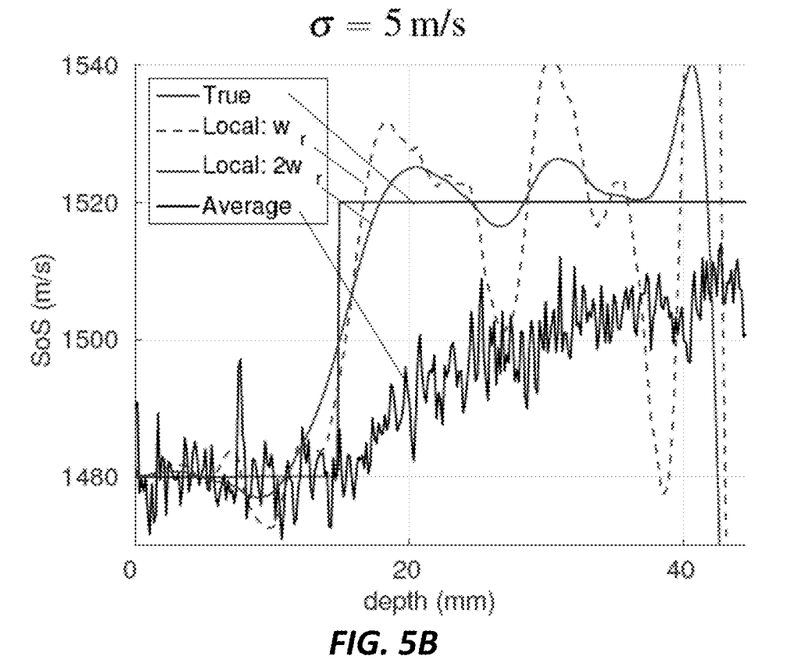

Plots in FIGS. 5A-5b show variations in the local SoS estimates caused by noise in the associated average SoS measurements. The average sound speeds are synthesized from true sound speed values using the forward model in (5). To facilitate interpretation of results, the SoS estimates are shown only along a single direction of wave propagation. When there is no noise in the synthetic data, the average and local SoS estimates behave in a similar way as in FIGS. 4A-4C; the average estimates increase gradually past the interface, and the local estimates are close to true SoS values. When noise is added to the synthetic data, the gradient descent solver increases the noise level, especially at large depths where less data is available for estimates. In particular, when added noise has a standard deviation of 5 m/s, the standard deviation of local SoS (computed between 20 and 40 mm depth) is 12.5 m/s. An L-norm regularization term has been used in the solver to help average the local SoS estimates and reduce their standard deviation back to 5.6 m/s.

Figure 6A:
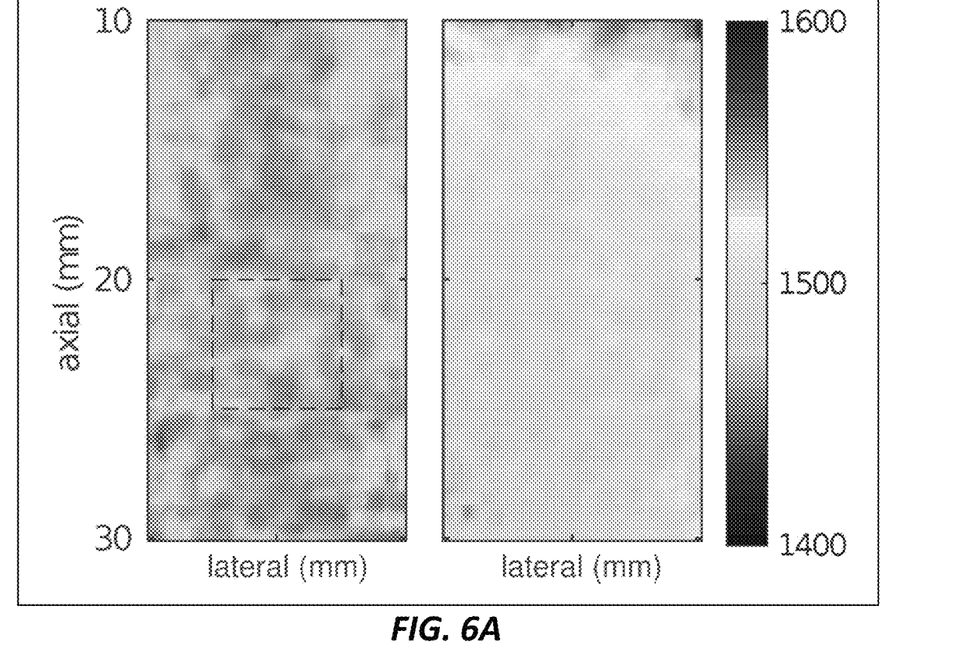
FIGS. 6A-6B show sound speed estimates from the simulated homogeneous media. (6A) The average SoS estimates computed via Anderson's method. (6B) The proposed local SoS estimator. From left to right true sound speeds of the simulated media are 1540, 1480, and 1600 m/s. The local SoS estimates are computed starting at 10 mm depth. The 5-by-5 mm region of interest used to compute the estimate statistics (Table III) is denoted using the dashed square, according to embodiments of the current invention.
Figure 6B:
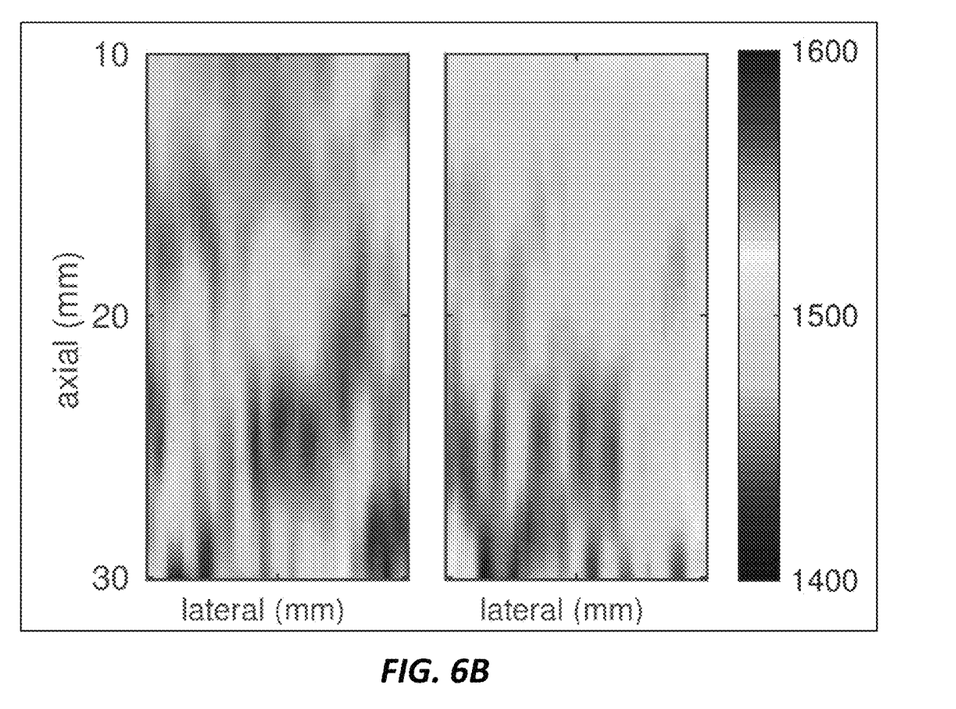
Figure 7:
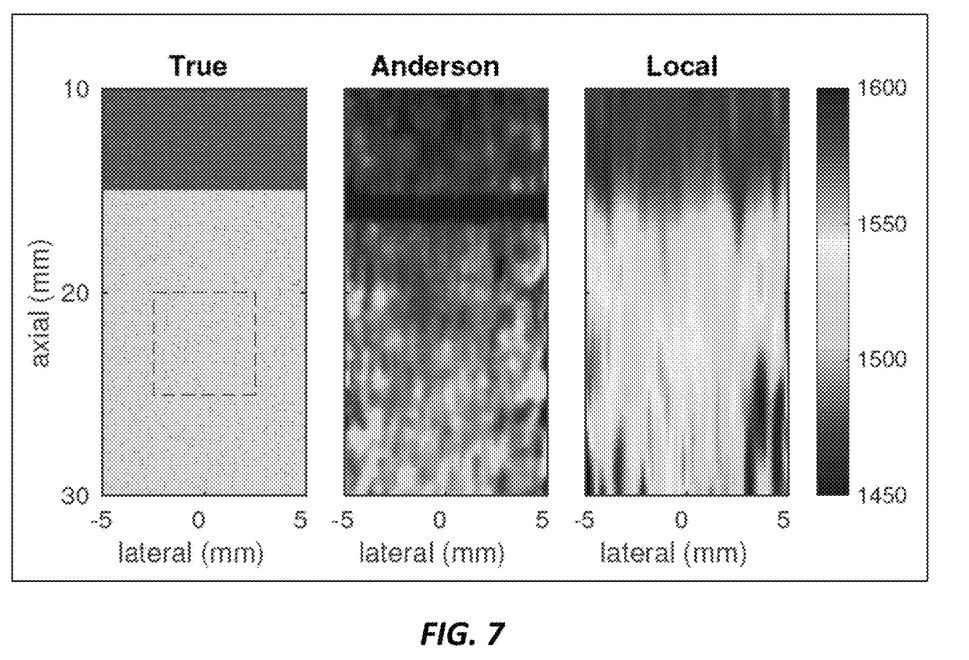
FIG. 7 shows example SoS maps of the simulated two-layer media. (left) Ground-truth speed of sound. (middle) The corresponding Anderson estimates. (right) The corresponding local sound-speed estimates. The local estimates in the bottom layer indicate lower bias than the corresponding Anderson estimates. The region of interest used to compute the estimate statistics is denoted with a red square. The estimate statistics for all the two-layer simulations is summarized in Table IV.

Regarding the results of the fullwave simulations, examples of SoS maps estimated from the simulated ultrasound signals are shown in FIGS. 6A-6B, and FIG. 7 for the homogeneous and two-layer media, respectively. For each map, reported herein is the SoS estimate averaged over a 5-by-5 mm ROI that is centered at 22.5 mm depth (the ROI is denoted with a dashed square in the first map of each Figure). To obtain estimate statistics, we compute the mean and standard deviation of the ROI-averaged SoS estimates across six different speckle realizations for each type of medium. These values are presented in Tables III and IV for the homogeneous and two-layer media, respectively. The standard deviation for an individual (per-point) SoS estimate is also computed within each ROI, and is reported under 'ROI Std dev' in both Tables.

TABLE III

Bias and standard deviation of estimates in simulated homogeneous media.

| | True Sound Speed | | | | | |
| --- | --- | --- | --- | --- | --- | --- |
| | 1540 m/s | | 1480 m/s | | 1600 m/s | |
| | Local | Anderson | Local | Anderson | Local | Anderson |
| mean | 1542.2 | 1535.9 | 1486.2 | 1475.2 | 1600.2 | 1598.4 |
| bias | 2.2 | −4.1 | 6.2 | −4.8 | 0.2 | −1.6 |
| Std dev | 4.0 | 0.8 | 6.5 | 1.4 | 4.7 | 1.5 |
| ROI Std dev | 11.1 | 5.0 | 12.8 | 6.3 | 17.6 | 8.7 |

TABLE IV

Bias and standard deviation of estimates in simulated two-layer media.

| | Sound Speed in Bottom Layer | | | | | |
| --- | --- | --- | --- | --- | --- | --- |
| | 1520 m/s | | 1540 m/s | | 1570 m/s | |
| | Local | Anderson | Local | Anderson | Local | Anderson |
| mean | 1524.7 | 1486.8 | 1538.7 | 1493.1 | 1571.5 | 1503.3 |
| bias | 4.7 | −33.2 | −1.3 | −46.9 | 1.5 | −66.7 |
| Std dev | 6.8 | 1.2 | 3.2 | 1.2 | 3.9 | 1.4 |
| ROI Std dev | 12.3 | 7.3 | 11.9 | 7.0 | 11.5 | 7.5 |

In FIGS. 6A-6B, displayed are the average (i.e. Anderson) and local SoS estimates for the simulated homogeneous media of different sound speeds. For all media, the local estimates display larger variation than the corresponding Anderson estimates. In addition, the variation of the local estimates seems to increase with depth, especially past 25 mm. These trends are confirmed by the estimate statistics in Table III. The local and Anderson estimates have comparable bias, which is less than 7 m/s for all maps. The standard deviations of the local estimates are also smaller than 7 m/s, but are larger than the standard deviations of the corresponding Anderson estimates (less than 2 m/s). The per-point (within ROI) standard deviation is also larger for the local estimates than for the Anderson estimates approximately by a factor of two, which is similar to the trend observed in the synthetic data in FIG. 5.

Examples of Anderson and local SoS estimates from a simulated two-layer medium are shown in FIG. 7. The leftmost map in the FIG. 7 displays true SoS values with the top layer of 1480 m/s and the bottom layer of 1520 m/s. Both Anderson and local estimates obtained from the top layer are close to true sound speed of 1480 m/s. The Anderson estimates from beyond 15 mm depth gradually increase (starting at 1480 m/s), which results in a large negative bias in the bottom layer. On the other hand, the local SoS map shows a clear separation between the two layers with estimates from the bottom layer closer to true SoS values. The bottom layer in the local SoS map appears noisier than the corresponding Anderson estimates.

The statistics of SoS estimates in Table IV support the observations in FIG. 7. Bias of the Anderson estimates is much larger than the bias of the local estimates and it increases with the difference in sound speed between the two layers. The smallest bias of the Anderson estimates is 33.2 m/s (computed for the 1480/1520 m/s map), while the largest bias of the local estimates is 4.7 m/s (computed for the same map). Furthermore, the standard deviations of the local estimates are larger than the standard deviations of the corresponding Anderson estimates, but none exceeds 7 m/s. Finally, the mean SoS estimates computed from the simulated ultrasound signals (Table IV) are similar to the mean sound-speed estimates obtained from the synthetic arrival-time profiles (Table II).

Figure 8A:
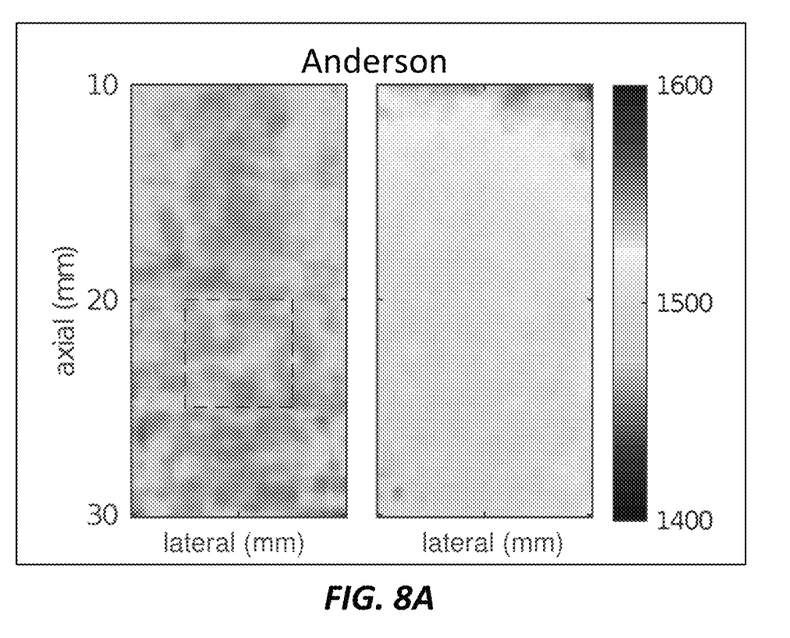
Figure 8B:
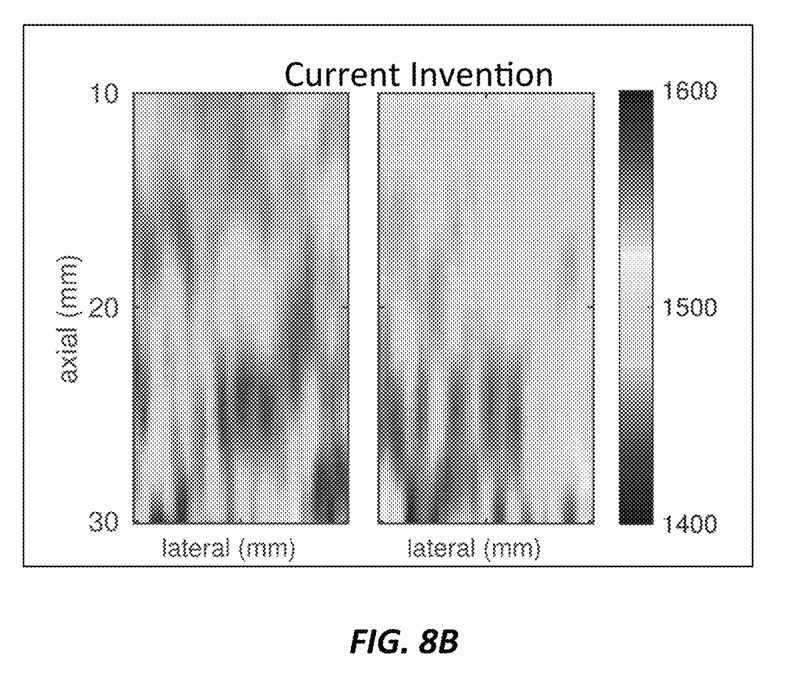

Regarding ex vivo experiments, the SoS estimates from the speckle phantom (with and without aberrating tissue layers) are shown in FIGS. 8A-8B and the corresponding estimate statistics is presented in Table V. From left to right, sound speed is estimated without an aberrator, with a 4 mm layer of porcine tissue, and with a 10 mm layer of porcine tissue placed on top of phantom. In the absence of an aberrator, both local and Anderson SoS estimates appear close to nominal speed of sound in the phantom (1460 m/s). When the ultrasound signals are acquired through a 4 mm layer of porcine tissue, the average SoS estimates at 10 mm depth are above 1500 m/s, and they gradually decrease with depth. The local SoS estimates on the other hand, are similar between the no-aberrator and the 4 mm-layer acquisitions, as confirmed by the corresponding mean estimates in Table V. When the data is collected through the 10 mm tissue layer, ultrasound signals are corrupt by reverberation clutter and the Anderson estimates appear noisy over top 20 mm. These noisy Anderson estimates are excluded from the gradient descent solver so the local estimates are displayed only between 20 and 30 mm depth (note that the average SoS measurements at 0-20 mm depth are corrupt by clutter and are thus omitted from the local SoS estimates here). For the 10 mm aberrator case, both Anderson and local SoS estimates are around 1500 m/s or higher (the corresponding mean values are 1499 m/s and 1510.7 m/s).

TABLE V

Bias and standard deviation of SoS estimates in the speckle phantom with and without aberrating layers in the acoustic path.

| | Aberrating Layer Thickness | | | | | |
| --- | --- | --- | --- | --- | --- | --- |
| | no aberrator | | 4 mm | | 10 mm* | |
| | Local | Anderson | Local | Anderson | Local | Anderson |
| mean | 1459.9 | 1466.1 | 1465.8 | 1494.5 | 1499.0 | 1510.7 |
| ROI Std dev | 13.6 | 5.0 | 11.1 | 6.5 | 12.2 | 9.7 |

Through these simulation and ex vivo experiments, SoS model and the associated local sound-speed estimator of the current invention was verified. Specifically, when average sound speeds are computed using the exact arrival times in two-layer media, the local sound speeds that are inferred from the model in (5) appear almost identical to true SoS maps (FIGS. 4A-4C). This can be explained by the following reasons. The average SoS measurements herein are obtained along a single direction of propagation, so the model matrix A, which encodes averaging (i.e. integration) of the local SoS values is a lower triangular matrix. Such system of equations has a single unique solution. In the absence of noise, the local sound speeds can be then estimated exactly, via direct differentiation of the adjacent measurements, or numerically (e.g. via gradient descent) with a high level of precision. When echo arrival-times are computed from the speckle targets, the Anderson SoS measurements are noisy, but the estimated local sound speed still conveys the structure of insonified media without significant artifacts (FIGS. 6A-6B and FIG. 7). In particular, the local SoS maps of simulated two-layer media display a clear boundary between the layers (FIG. 7). Regularization term in the gradient descent solver is used to restrict the noise level of the final local SoS estimates (FIG. 5).

Local sound-speed estimates exhibit low bias in the presence of inhomogeneities compared to the matching Anderson estimates. In the homogeneous media, the bias of the local SoS estimates is not larger than 6.2 m/s (depending on the medium) and is comparable to the bias of Anderson estimates (Table III). In the two-layer media, the bias of local SoS estimates from the bottom layers is lower by up to 60 m/s than the bias of matching Anderson estimates and is generally unaffected by the sound-speed of the top layer (Tables II and IV). This trend can be explained by equation (5), which models Anderson (i.e. average) sound-speed as an average of local sound-speeds along the propagation path. Therefore, the bias of the Anderson estimates from bottom layers is expected to increase with the difference in sound-speed between the two layers. On the other hand, the local sound-speed is computed by taking a difference of average sound-speed measurements, which is expected to annul their individual biases (caused by preceding layers in the propagation path). Note: If inhomogeneities along the propagation path cause strong reverberation and noise in the average SoS measurements, the resulting local SoS estimates may suffer from increased bias and standard deviation.

TABLE VI

Lag-one normalized cross-correlation (ρ) and rms error of parabolic fit to squared arrival-times in the speckle phantom with and without tissue layers in the acoustic path.

| Aberrating Layer | no aberrator | 4 mm | 10 mm |
| --- | --- | --- | --- |
| ρ mean | 0.974 | 0.965 | 0.912 |
| ρ Std dev | 0.0008 | 0.010 | 0.014 |
| RMS error ($s^2$) | $1.25 \times 10^{-13}$ | $1.57 \times 10^{-13}$ | $4.48 \times\times 10^{-13}$ |

The local sound-speed estimator of the current invention increases the standard deviation of input measurements (i.e. average SoS). Specifically, going from average to local SoS in the simulated media and the phantom the standard deviation of individual estimates increases approximately by a factor of two (denoted as 'ROI Std dev' in Tables III, IV, and V2). As stated earlier, because the model matrix A in equation (5) is an integration operator, solving for the local SoS implies differentiation of Anderson measurements, which increases the noise level. If no regularization is employed and the Anderson measurements are independent, the standard deviation of the resulting local estimate can be predicted as $\sqrt{2}N_A\sigma$, where $N_A$ is the number of Anderson measurements collected along a single direction of wave propagation, and a is the standard deviation of an individual Anderson estimate. In other words, the proposed local estimator accumulates measurement error with depth. In practice, vertically adjacent Anderson measurements show modest correlation as their associated wave propagation paths overlap; this causes a decrease in standard deviation of the local estimates from the levels predicted by the above equation.

The speed of sound reported herein is the mean local estimate over a 5-by-5 mm ROI. The standard deviation of ROI-averaged local SoS (denoted as 'Std dev') is measured to be two to three times smaller than the standard deviation of individual local estimates (Tables III and IV). The exact extent of noise-reduction achieved by ROI-averaging is specific to the acquisition setup employed and depends on factors such as the amount of beam overlap from the adjacent average SoS measurements and the level of regularization used in axial dimension.

Figure 9A:
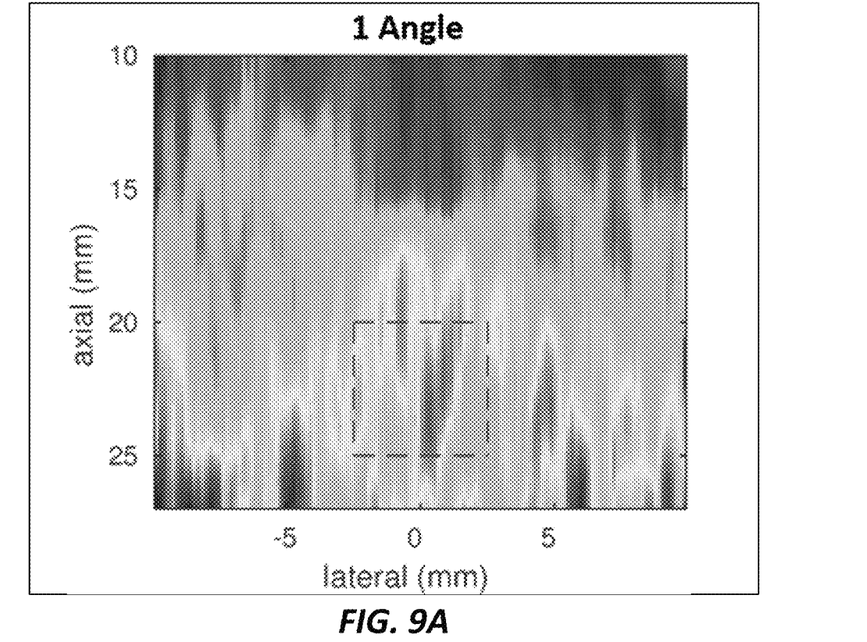
FIGS. 9A-9B show (9A) the local sound speed estimated from the fullwave simulation of the two layer phantom. These local sound speeds are computed using a single angle (0 degrees) of wave propagation and a single model matrix. (9B) shows, a model equation is created for each of 5 angles (−10, −5, 0, 5, and 10 degrees) and each model equation is solved individually for the local speed of sound. The local speed of sound estimates from each angle is then averaged, which reduces the standard deviation of the local sound speed estimate compared to a single angle, according to embodiments of the current invention.
Figure 9B:
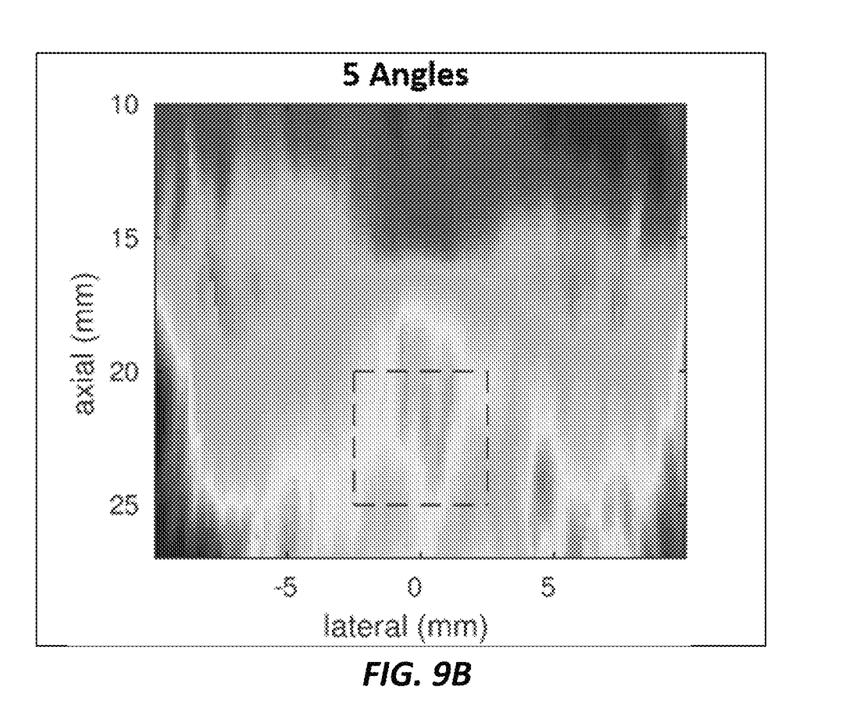

To reduce the standard deviation of local estimates and enable their potential use in clinic, additional information can be employed, such as estimation of local speed of sound from multiple angles. FIG. 9 shows a comparison between the local estimates derived from one angle of wave propagation and the local estimates derived from averaging individual computations from 5 angles. In FIG. 9, the fullwave simulated ultrasound signals from the 3 two-layer phantoms were used to reduce the ROI standard deviation of the local estimates in Table IV to 7.0, 8.5, and 7.9 m/s for the phantoms with 1520, 1540, and 1570 m/s in the bottom layers, respectively.

While the local estimator of the current invention produces accurate sound-speed estimates in the presence of mild noise, its performance can be compromised when ultrasound signal is corrupt by strong reverberation clutter. In particular, the local SoS estimates from the speckle phantom are similar when the data is collected directly on the phantom and through a 4 mm tissue layer (FIGS. 8A-8B and Table V). However, in the presence of a 10 mm tissue layer, the mean of local estimates is 40 m/s higher than for the no-tissue case (Table V). As the level of acoustic noise increases, the arrival-time estimates become less accurate, which in turn diminishes accuracy of Anderson and local SoS estimates. Large error in estimated arrival times for the 10 mm-tissue case is reflected in lower lag-one correlations values (measured across the individual-element signals) and decreased quality of the parabolic fit to the squared arrival-time profiles. These metrics are summarized for all phantom acquisitions in Table VI. To improve the method's performance in the presence of strong clutter, clutter reduction techniques that preserve the individual-element signals may be used. In addition, a focused transmit can be used (instead of synthetic aperture acquisition) to increase the ratio of signal to electronic noise and to allow the use of data from larger depths, where reverberation clutter is reduced.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. Alternative methods for determining the average speed of sound, element delays, solver, and regularization can be utilized with the model equations (5a) and (5b). For example, the element delays can be solved using phase delay estimators, such as the 2D autocorrelator method proposed by Loupas et al., or using quality factors other than cross-correlation, such as sum-of-absolute-differences. The solution to the model equations (5a) and (5b) could be solved with regularizations of different norms to reduce noise or improve image sharpness. A generalized version of this solution are equations of the form $\underline{c}_{avg}=A\underline{c}_{local}+\varepsilon_{meas}$, $0=D\underline{c}_{local}+\varepsilon_{diff}$. In this context, the numerical solver minimizes a quantity $$\left\| \begin{pmatrix} \varepsilon_{meas} \\ \varepsilon_{diff} \end{pmatrix} \right\|_p ,$$

where the two error vectors are concatenated together and the $l_p$ norm of this vector is minimized. Minimization with the $l_2$ norm is a least squares problem and may be preferred for its computational efficiency. Minimization with the $l_1$ norm is a total variation problem and may be preferred to improve image sharpness. Minimization of $|\varepsilon_{meas}|_p+|\varepsilon_{meas}|_q$, with p and q defining two separate norms, is also a possibility. In addition, weighting different measurements and solving a weighted least squares problem could be performed if it is known that some measurements have lower expected noise.

All such variations are considered to be within the scope and spirit of the present invention as defined by the following claims and their legal equivalents.

What is claimed:

1. A method implemented by a pulse-echo ultrasound system of measuring local speeds of sound for medical ultrasound, comprising:
   a) inducing ultrasound waves in a subject under test by focusing an ultrasound beam at a region of interest, using an ultrasound Tx transducer, wherein said ultrasound waves propagate from an ultrasound Tx focal point to a surface of said subject under test;
   b) measuring pulse-echo data using at least three single ultrasound Rx transducer elements disposed on said surface of said subject under test, and estimating from the pulse-echo data average speeds of sound along a propagation path of said ultrasound waves from the ultrasound Tx focal point to the surface;
   c) computing local speeds of sound ($c_i$) along multiple points of wave propagation paths of said ultrasound waves from the estimated average speeds of sound ($c_{avg}$) using a model wherein said $c_{avg}$ equals an arithmetic mean of said $c_i$ values sampled along a wave propagation path according to $$c_{avg} = \frac{1}{N}\sum_{i=1}^{N} c_i,$$

wherein said $c_i=d_i/T_s$, wherein said $d_i$ is a length of a tissue segment traveled during one sampling period $T_s$; wherein computing the local speeds of sound is performed by solving a system of linear equations relating the local speeds of sound to the estimated average speeds of sound; and
   d) using the computed local speeds of sound to reconstruct a B-mode ultrasound image or to differentiate states of disease.

2. The method according to claim 1, wherein signal traces recorded on the ultrasound Rx transducer elements are uniformly sampled in space, and in the model an average slowness in said subject under test equals an arithmetic mean of local slowness values sampled along a propagation path of said ultrasound.

3. The method according to claim 1, wherein estimating from the pulse-echo data average speeds of sound comprises fitting a parabolic profile to times of arrival in the measured pulse-echo data, that defines a geometric distance from said ultrasound Tx focal point to at least three single ultrasound Rx transducer elements.

4. The method according to claim 1, further comprising computing an arrival-time profile of said propagating ultrasound waves across all said ultrasound Rx transducer elements from times of arrival determined by a multi-lag least-squares estimation algorithm.

5. The method according to claim 1 wherein an arrival-time profile of said propagating ultrasound waves is determined from elements of said Tx transducer.

6. The method according to claim 1 wherein measuring pulse-echo data comprises measuring times of arrival.

7. The method according to claim 1, wherein the model comprises a system of linear equations $\underline{c}_{avg}=A\underline{c}_{local}+\varepsilon_{meas}$, wherein each row of a model matrix A encodes a single measurement of said average speeds of sound in vector $c_{avg}$, wherein a vector $c_{local}$ contains said local speeds of sound $c_i$ to be solved for, wherein $\varepsilon_{meas}$ is a vector of measurement errors to be minimized.

8. The method according to claim 7, wherein a gradient descent algorithm is used to solve the system of linear equations.

9. The method according to claim 7, wherein said matrix A is triangular and a direct inversion is used to solve the system of linear equations.

10. The method according to claim 7, wherein said matrix A encodes relationships between the average speeds of sound and the local speeds of sound.

11. The method according to claim 7, where $c_{local}$ is solved for using multiple directions of propagation.

12. The method according to claim 7, where said minimization of said vector of measurement $\underline{\varepsilon}_{meas}$ is performed with the $l_1$ norm or $l_2$ norm.

13. The method according to claim 7, wherein image noise is reduced by using additional regularization of the spatial variation of said $c_{local}$.

\* \* \* \* \*